United States Patent [19]
Leonard

[11] Patent Number: 5,152,964
[45] Date of Patent: Oct. 6, 1992

[54] MEMBRANE BLOOD OXYGENATOR

[75] Inventor: Ronald J. Leonard, Ann Arbor, Mich.

[73] Assignee: Minnesota Mining and Manufacturing Company, St. Paul, Minn.

[21] Appl. No.: 657,338

[22] Filed: Feb. 15, 1991

Related U.S. Application Data

[63] Continuation of Ser. No. 284,092, Dec. 14, 1988, abandoned.

[51] Int. Cl.⁵ .............................................. A61M 1/14
[52] U.S. Cl. .................................... 422/48; 55/16; 55/158; 128/DIG. 3; 261/DIG. 28
[58] Field of Search ............... 422/45, 48; 55/16, 158; 128/DIG. 3; 261/DIG. 28

[56] References Cited

U.S. PATENT DOCUMENTS

| | | | |
|---|---|---|---|
| 3,526,481 | 9/1970 | Rubricius | 23/258.5 |
| 3,717,174 | 2/1973 | Dewall | 422/48 X |
| 3,794,468 | 2/1974 | Leonard | 23/258.5 |
| 3,927,980 | 12/1975 | Leonard | 128/DIG. 3 |
| 4,572,446 | 2/1986 | Leonard et al. | 242/7.02 |
| 4,690,758 | 9/1987 | Leonard et al. | 210/247 |
| 4,735,775 | 4/1988 | Leonard et al. | 422/46 |
| 4,767,289 | 8/1988 | Parrott et al. | 417/477 |

Primary Examiner—Lynn M. Kummert
Attorney, Agent, or Firm—Gary L. Griswold; Walter N. Kirn; Jeffrey J. Hohenshell

[57] ABSTRACT

A membrane blood oxygenator having a mechanism for automatically maintaining the total pressure of the oxygenating gas near yet below that of the blood across the membrane is described. This includes a valve for restricting the flow of oxygenating gas exiting the oxygenator with the pressure of the blood exiting the oxygenator. A tubing communicates the pressure of the exiting blood to the valve to activate the valve.

12 Claims, 3 Drawing Sheets

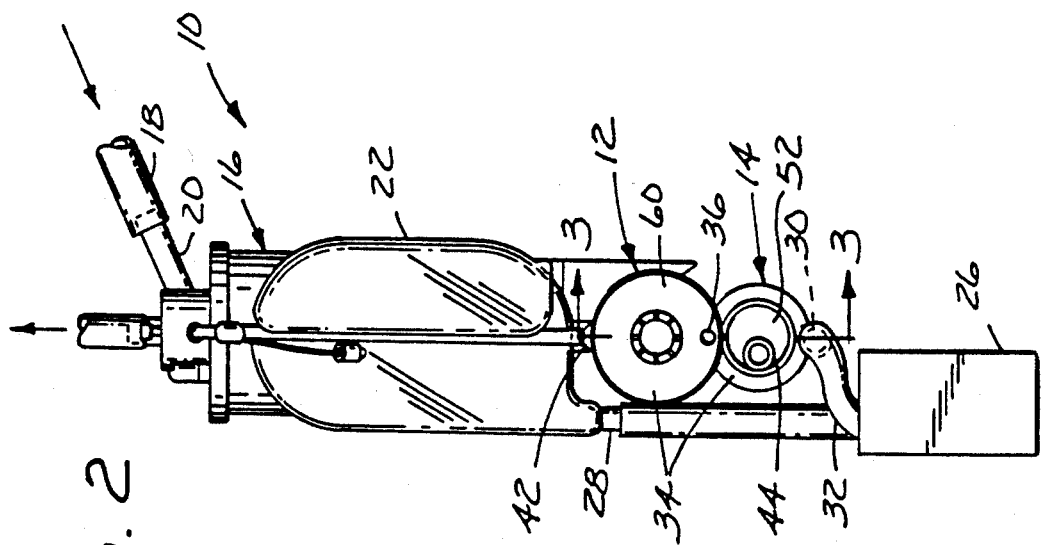
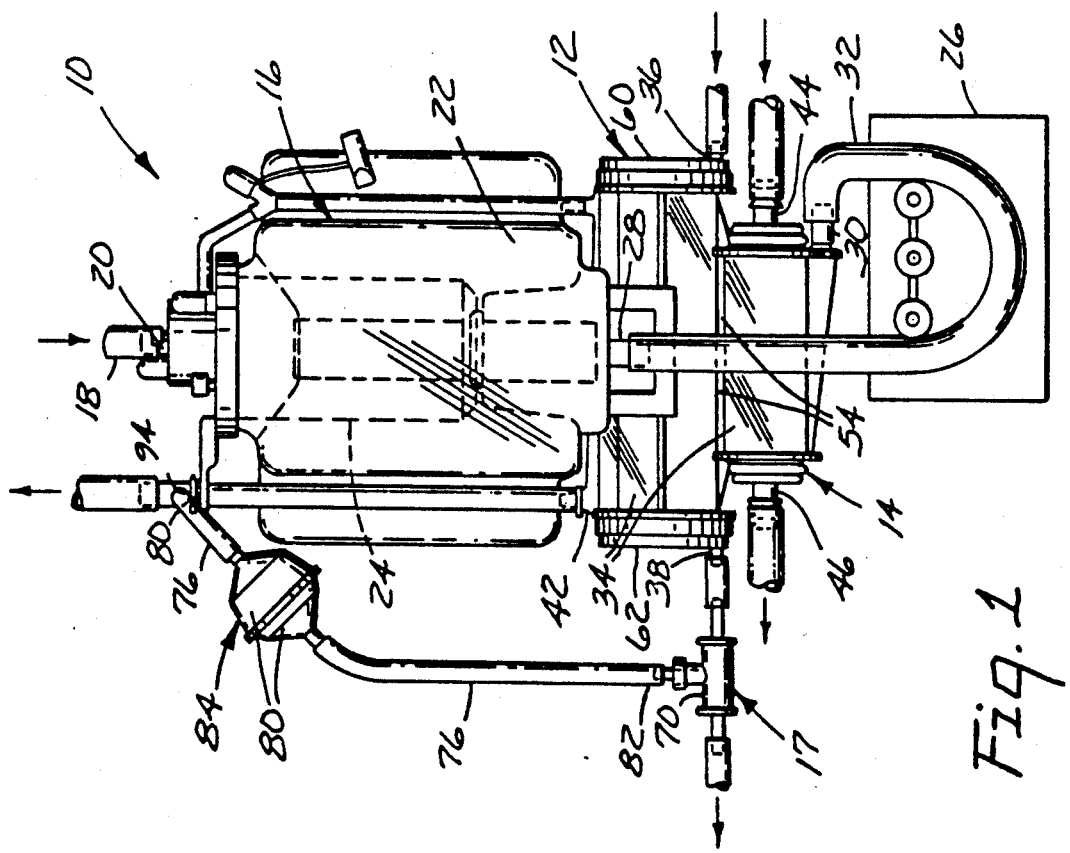

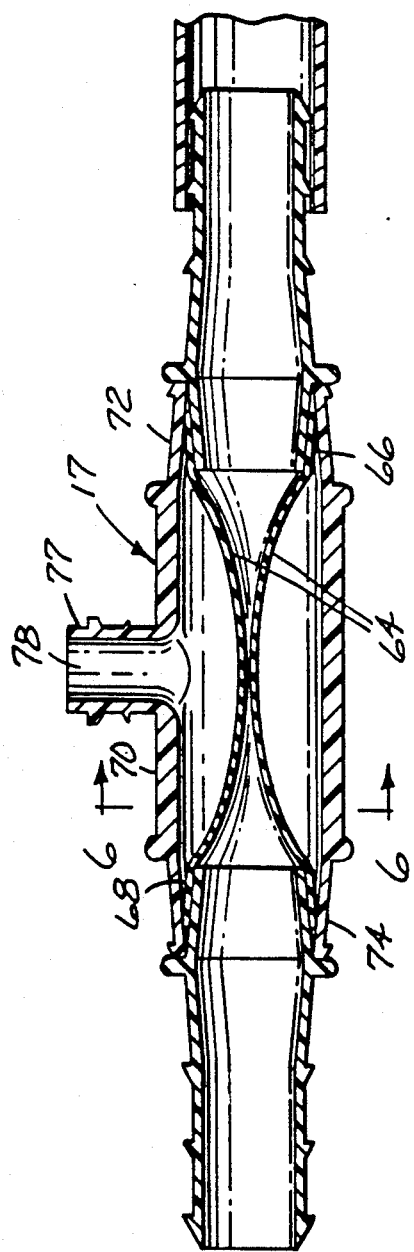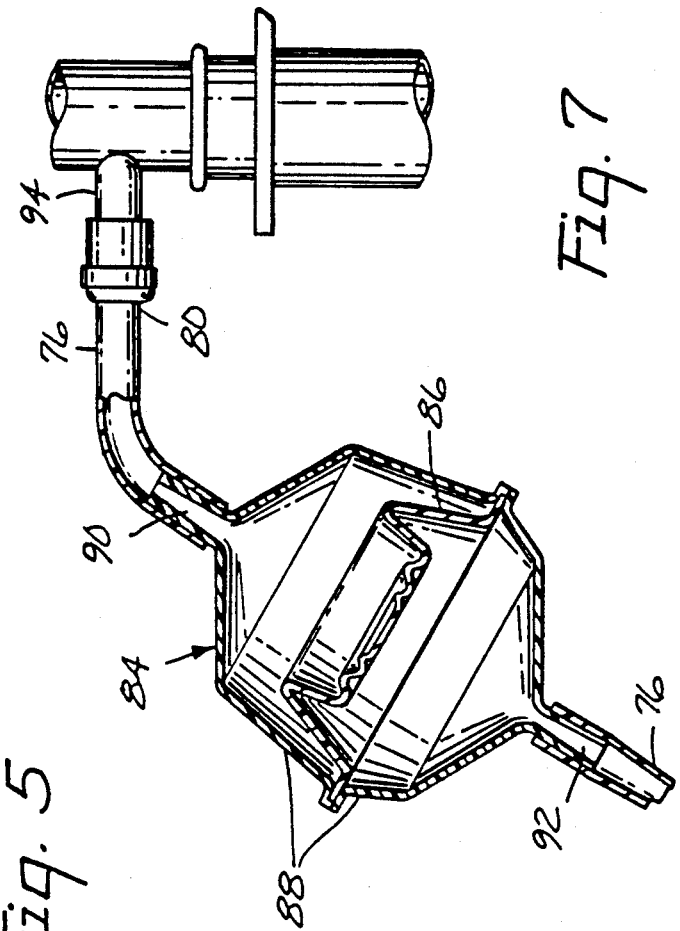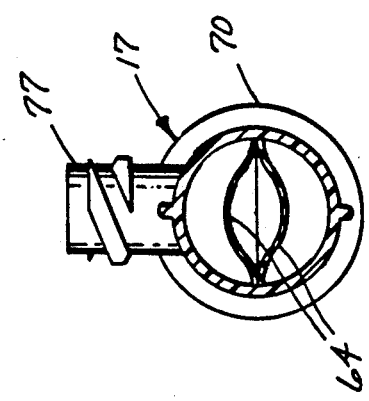

MEMBRANE BLOOD OXYGENATOR

This is a continuation of application Ser. No. 07/284,092, filed Dec. 14, 1988, now abandoned.

FIELD OF THE INVENTION

This invention relates to extracorporeal life support systems and particularly to extracorporeal membrane blood oxygenators for oxygenating a patient's venous blood prior to returning this blood to a patient's arterial system.

BACKGROUND ART

Extracorporeal blood oxygenators are widely used to add oxygen to and remove carbon dioxide from a patient's blood during those times when the patient's lungs do not satisfactorily perform this gas exchange function. One example of such a time is during coronary artery bypass graft surgery when the cardiac activity is electively stopped to facilitate the surgery. To perform this function for the lungs, the venous blood is drained from the heart into an extracorporeal oxygenator, oxygenated and returned to the aorta for recirculation throughout the patient's body.

Several types of oxygenators are available. Among these is the membrane oxygenator. A membrane oxygenator, in its basic form, comprises first and second conduits separated by a transfer membrane which is permeable to oxygen and carbon dioxide. During use of the membrane oxygenator, an oxygenating gas is caused to pass through one of the conduits while the patient's blood is caused to flow through the other conduit. Oxygen passes from the oxygenating gas through the transfer membrane and into the blood. Simultaneously, carbon dioxide passes from the blood through the transfer membrane and into the oxygenating gas.

One known way to improve the performance of these membrane oxygenators is to simply provide more membrane surface area. Another known way to improve the performance of membrane oxygenators is to increase the amount of gas transfer per unit of transfer membrane surface area by improving blood mixing over the membrane surface. Some of the highest gas transfer rates for membrane blood oxygenators are believed to be associated with hollow fiber membrane oxygenators as described, for example, in U.S. Pat. Nos. 4,690,758 and 4,735,775. In these oxygenators, the oxygenating gas flows through the hollow fibers and the patient's blood flows around the hollow fibers.

Another known way to improve the performance of membrane oxygenators is to vary the partial pressure difference of the diffusing oxygen and carbon dioxide on opposite sides of the membrane. However, a limiting factor at least with respect to microporous hollow fiber membrane oxygenators is the need to maintain the total pressure of the oxygenating gas at each place within the oxygenator generally at or below the total pressure of the blood opposite the membrane within the oxygenator to avoid bubbling the oxygenating gas into the blood with the attendant risks associated with a gas embolism. Avoidance of the formation of gas bubbles within the blood is complicated by, among other things, the variance of the blood pressure and the variance of the gas pressure within the oxygenator. These pressures are reflective of the differing oxygen and carbon dioxide needs of different patients and the differing needs of a single patient over time. Efforts in the past to maintain the total pressure of the oxygenating gas below that of the blood across the membrane have included simply venting the outlet of the oxygenating gas to atmosphere through a relatively low pressure drop gas path.

SUMMARY OF THE INVENTION

The present invention provides a membrane blood oxygenator having fail-safe means for automatically maintaining the total pressure of the oxygenating gas near yet below that of the blood across the membrane. In the preferred embodiment, the oxygenator comprises a housing having a hollow portion receiving a hollow fiber bundle defining oxygenating gas flow paths inside the fibers and means for automatically maintaining the total pressure of the oxygenating gas at each place within the bundle near yet below the total pressure of the blood opposite the bundle generally throughout the bundle. The automatically maintaining means comprises means for restricting the flow of oxygenating gas exiting the oxygenator with the pressure of the blood exiting the oxygenator and preferably includes a valve member and tubing communicating the pressure of the exiting blood to the valve member to activate the valve member.

BRIEF DESCRIPTION OF THE DRAWING

The invention is illustrated in the accompanying drawing wherein like numbers refer to like parts.

FIG. 1 is a front elevational view of the extracorporeal device of the preferred embodiment of the present invention.

FIG. 2 is a side elevational view of the device of FIG. 1.

FIG. 5 is an enlarged vertical sectional view of a valve member of the device of FIG. 1 that can restrict the flow of oxygenating gas exiting the device of FIG. 1.

FIG. 6 is a sectional view taken approximately along the line 6—6 of FIG. 5.

FIG. 7 is an enlarged elevational view of a fluid transducer of the device of FIG. 1 that can communicate the pressure of blood exiting the device of FIG. 1 to the valve member of FIGS. 1, 5 and 6 to restrict the flow of oxygenating gas exiting the device of FIG. 1.

DETAILED DESCRIPTION

Figure 4:
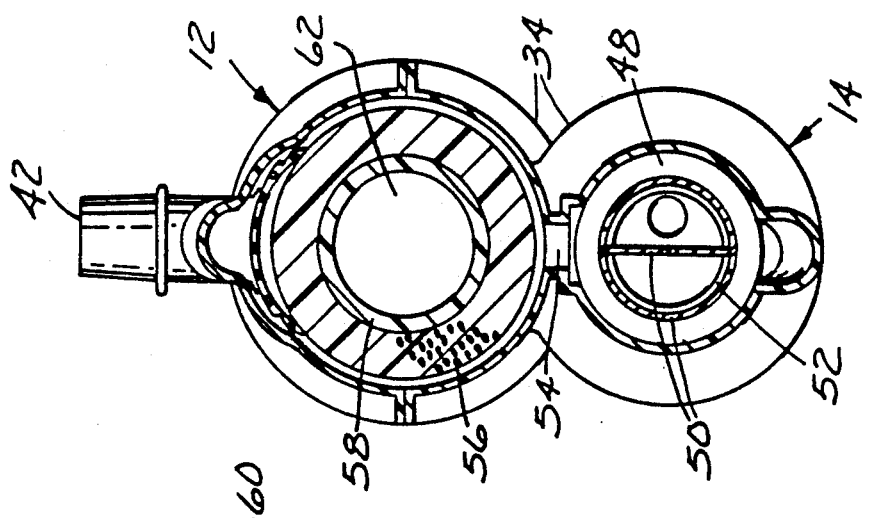
FIG. 4 is a sectional view taken approximately along the line 4—4 of FIG. 3.

Referring to the figures of the drawing, there is shown in FIGS. 1 and 2 an extracorporeal device 10 of the preferred embodiment of the present invention generally comprising a hollow fiber membrane oxygenator 12, a heat exchanger 14, a venous reservoir 16, and a valve 17 for pressurizing the oxygenating gas. The preferred device 10 mounts on a Sarns Oxygenator Unit Bracket, part number 164490, available from Sarns Inc, Ann Arbor, Mich., U.S.A. The preferred device 10 is used with a Sarns Oxygen-Air Blender, part number 164235, also available from Sarns Inc. The venous reservoir 16 debubbles, filters and stores venous blood prior to oxygenation. The oxygenator 12 adds oxygen to and removes carbon dioxide from the blood. The heat exchanger 14 heats or cools blood. A suitable combination reservoir, oxygenator and heat exchanger is available from Sarns Inc as part number 16385.

The venous blood is drained from a patient in conventional fashion and delivered to the device 10 through medical-grade tubing 18. The tubing 18 is suitably attached to a conventional blood inlet 20 in fluid communication with the venous reservoir 16 so that the venous blood can pass into the body 22 via the blood defoamer and/or filter 24.

When a conventional blood pump 26 is activated, the blood is drawn from an outlet 28 of the reservoir 16 and delivered to an inlet 30 of the heat exchanger 14 through medical-grade tubing 32. Suitable blood pumps are available from Sarns Inc. In the preferred embodiment, the heat exchanger 14 and the oxygenator 12 are disposed in a housing 34. This housing 34 includes a first fluid inlet 36 which is used as an oxygenating gas inlet, a first fluid outlet 38 which is used as an oxygenating gas outlet, a second fluid inlet 30 which is used as a blood inlet, a second fluid outlet 42 which is used as a blood outlet, a third fluid inlet 44 which is used as a heat transfer fluid inlet, and a third fluid outlet 46 which is used as a heat transfer fluid outlet.

Figure 3:
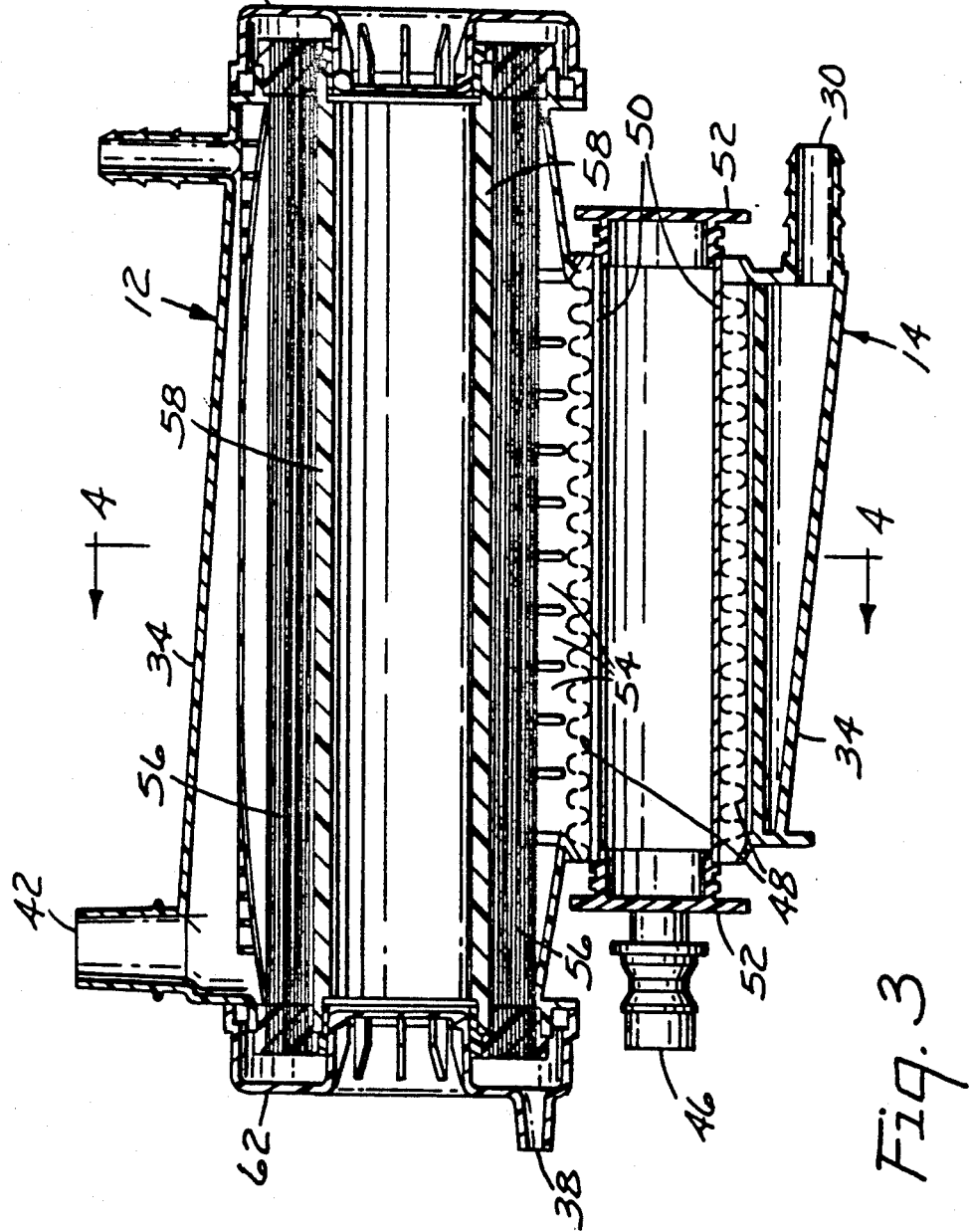
FIG. 3 is an enlarged sectional view taken approximately along the line 3—3 of FIG. 2.

Referring to FIGS. 3 and 4, the heat exchanger 14 includes a core 48, a manifold 50, end caps 52, inlet 44 and outlet 46. A passageway 54 couples the heat exchanger 14 with the outside of a microporous, hollow fiber bundle 56 within the oxygenator 12. The bundle 56 is wound about a plastic core 58 as is well known in the art. See, for example, U.S. Pat. Nos. 4,735,775, 4,690,758, 4,572,446 and 3,794,468. The hollow fiber bundle 56 is encapsulated at its ends by means of a potting compound, although the ends of the hollow fibers are open to form oxygenating gas flow paths as is known in the art. End caps 60 and 62 secure the ends of the oxygenator 12.

The blood path is into the second inlet 30, around the outside of the heat exchanger core 48 where the blood is heated or cooled, as the case may be, along the passageway 54 to the oxygenator 12, around the individual fibers of bundle 56 where the blood is enriched with oxygen and finally out of the second outlet 42. The heat transfer fluid, typically water, follows a path via the third inlet 44, through the heat exchanger manifold 50 and core 48 and out the third outlet 46. The oxygenating gas path is into the first inlet 36, through the individual fibers of bundle 56 and out the first outlet 38. The first, second and third inlets and outlets are of conventional design so that the oxygenating gas and water can be supplied from conventional sources.

Referring now to FIGS. 1, 2, 5, 6 and 7 and in particular to FIG. 5, there is shown the valve 17 for pressurizing the oxygenating gas. The valve 17 includes an inner tube 64 having an inlet 66 and an outlet 68, a housing 70, an inlet portion 72, an outlet portion 74 and means for maintaining an above-ambient pressure in the area between the housing 70 and the inner tube 64. The inner tube 64 is received within the housing 70. The inlet portion 72 connects the housing 70 to the inner tube 64 adjacent the inlet 66 of the inner tube 64. The outlet portion 74 connects the housing 70 to the inner tube 64 adjacent the outlet 68 of the inner tube 64. The inner tube 64 is preferably relatively soft and flexible and comprised of a thin walled vinyl, urethane or silicone rubber material conventionally heat sealed along two longitudinally aligned, parallel edges and having a wall thickness in the range of about 0.001-0.020 inches. The inner tube 64 preferably is sufficiently soft and flexible to offer little or no resistance to externally applied pressures; i.e., the inner tube 64 freely opens and closes in cross section in response to pressure differences between the inside and the outside of the tube 64. The housing 70 is preferably comprised of a relatively rigid polycarbonate or acrylic plastic material.

The means for maintaining the above-ambient pressure in the area between the housing 70 and the inner tube 64 includes a tubing 76 communicating the pressure of the blood exiting the oxygenator 12 to the area between the housing 70 and the inner tube 64. The housing 70 has a portion 77 having an aperture 78 there through. The tubing 76 has an inlet 80 in fluid communication with the second outlet 42 of the housing 34 and the tubing 76 has an outlet 82 in fluid communication with the aperture 78 through the housing 70 of the valve 17 so that the pressure in the area between the housing 70 and the inner tube 64 approaches that of the exiting blood at the inlet 80 of the tubing 76. Preferably, the blood does not directly occupy the area between the housing 70 and the inner tube 64. This avoids possible over-pressurization of the valve 17 by a column of blood in the tubing 76. Instead, a fluid transducer 84 communicates the exiting blood pressure to the area between the housing 70 and the inner tube 64 via a diaphragm 86.

Referring specifically to FIG. 7, the transducer 84 generally comprises a two-piece housing 88 enclosing and supporting the diaphragm 86. A suitable transducer is a pressure isolator available from Gish Biomedical, Inc., Santa Ana, Calif., U.S.A. The transducer 84 includes an inlet 90 in fluid communication with the inlet 80 of the tubing 76 and an outlet 92 in fluid communication with the outlet 82 of the tubing 76. The portion of the tubing 76 between the transducer 84 and the valve 17 can be filled with air or another suitable fluid. The tubing 76 is connected to a fluid access port 94 at a vertical distance with respect to gravity from the second outlet 42 of the housing 34 of the oxygenator 12.

The operation of the extracorporeal device 10 will next be described with reference generally to the figures of the drawing. As noted earlier, the device 10 is preferably connected to the oxygen-air blender in conventional fashion at the first inlet 36. Similarly, the device 10 is preferably connected to a conventional source of heated or cooled water at the third inlet 44. After these connections have been made and adjusted to the user's satisfaction, the pump 26 is activated, and blood is drawn from the body 22 of the reservoir 16 and delivered to the second inlet 30. From the second inlet 30, the blood is pumped through the heat exchanger 14 where it is suitably heated or cooled, passed through the passageway 54, and on to and through the oxygenator 12 where oxygen/carbon dioxide exchange takes place. Finally, the blood is pumped out the second outlet 42 and past the fluid access port 94.

The fluid access port 94 is preferably disposed a predetermined vertical distance with respect to gravity from the outlet 42 sufficient to ensure that the blood pressure at the inlet 80 will be near yet below the blood pressure of the blood at each place within the oxygenator 12. The blood pressure at the inlet 80 of the tubing 76 is preferably in the range of about 0-500 mmHg above ambient atmospheric and most preferably is about 300 mmHg.

The blood pressure at the inlet 80 of the tubing 76 is communicated to the blood side of the diaphragm 86 of the fluid transducer 84 through the inlet 90 of the transducer 84. This pressure deforms or otherwise moves the diaphragm 86 to pressurize a suitable fluid in the lower portion of the tube 76, which in turn communicates this pressure to the valve 17. Assuming a negligible head height difference between the inlet 80 and the transducer 84 and the usage of a suitably light fluid such as air in the lower portion of the tubing 76, the pressure communicated to the valve 17 will closely approximate that present at the inlet 80.

The pressure communicated to the valve 17 is communicated to the area between the housing 70 and the inner tube 64 through the aperture 78. As noted earlier, this pressure is most preferably about 300 mmHg. This pressure tends to urge the inner tube 64 to close against the pressure of the oxygenating gas exiting the first outlet 38 of the device 10. This urging, in turn, raises the pressure of the oxygenating gas exiting the first outlet 38 to approximately that of the blood at the fluid access port 94, assuming a negligible pressure drop across the valve 17. Assuming a negligible pressure drop across the oxygenator 12, this raises the pressure of oxygenating gas within the oxygenator 12 to near yet below the blood pressure at the fluid access port 94, which is near yet below the total blood pressure opposite the bundle 56 of the oxygenator 12 generally throughout the bundle 56. Whatever pressure drops that do exist between the fluid access port 94 and the bundle 56 through the route of the tubing 76 will only greater ensure that the pressure of the oxygenator gas at each place within the bundle 56 is below the total pressure of the blood opposite the bundle 56 generally throughout the bundle 56.

The pressure of the oxygenating gas is self-regulating to stay near yet below the blood pressure due to the construction, location and operation of the tubing 76 together with the transducer 84 and the valve 17. In operation, there is a positive pressure at access port 94 due to the blood flow provided by pump 26 and the resistance of the rest of the system. Typically this pressure may range from 100 to 500 mmHg above ambient depending upon the selection and size of the individual items of the extracorporeal life support system, the vascular state of the patient, and the blood flow rate. It is known that the transfer rate of a gas into a liquid such as blood is a function of the partial pressure driving force between the gas and the liquid and not the liquid pressure itself. Hence, as the blood flow increases, normally indicating increased patient oxygen demand, the oxygen transfer will be automatically increased as the higher flow is reflected as a higher pressure to the gas path by means of the tubing 76, transducer 84 and valve 17. As the blood flow decreases, the opposite happens.

Carbon dioxide transfer may actually be impaired by the action of this invention, since the partial pressure of the carbon dioxide in the gas path will also be increased by the action of increasing the gas path pressure. However, membrane oxygenators employing microporous membranes generally have carbon dioxide transfer rates at high gas flows which are substantially higher than their oxygen transfer capabilities. In that sense the device 10 of the present invention actually helps in that it tends to moderate the imbalance in transfer rates. Additionally, patients normally produce carbon dioxide at a rate lower than their oxygen consumption as reflected in the respiratory quotient. This is the ratio of carbon dioxide production to oxygen consumption and is generally on the order of about 0.8.

The action of the device 10 of this invention can be moderated in several ways. The percent oxygen in the oxygenating gas can be used to trim the oxygen transfer rate as is now done with standard oxygenators. The arterial line might actually be restricted using a Harvard clamp or the like to increase the arterial line pressure and thereby further increase the performance of the oxygenator. This could be done on a temporary basis in case of some transient high oxygen demand from the patient. Also, valve 17 can be effectively eliminated by closing a valve (not shown) at the access port 94 and venting the pressure at outlet 38 to interrupt the action of the gas pressure control and return to normal atmospheric operation. This might be done during times of minimal oxygen demand such as at very low patient temperatures, where the patient metabolic rate is very low.

The operation of the above-described device 10 can perhaps be better understood with reference to the following examples. The first example uses the standard Sarns oxygenator, part number 16385 as identified earlier. This oxygenator exhibits a blood outlet oxygen partial pressure of approximately 80 mmHg when operated with a blood inlet oxygen partial pressure of 35 mmHg with normal standard blood at 6 liters per minute of blood flow. When the oxygenator is equipped with the tubing 76, transducer 84 and valve 17 of the device 10 of the present invention and is used at an arterial line blood pressure of about 300 mmHg, and therefore a similar increase in the gas pressure by way of the invention, the outlet oxygen partial pressure in the blood is 215 mmHg. This indicates that the device 10 of this invention improves the performance of a conventional hollow fiber membrane oxygenator.

For the second example, a second oxygenator was constructed similar to the standard Sarns oxygenator, but with a fiber area of only 1.0 square meters as opposed to 1.8 square meters for the standard device. Operated under the conditions of the first example, the blood outlet oxygen partial pressure was only about 66 mmHg without the addition of the tubing 76, transducer 84 and valve 17 as would be expected due to the reduced surface area for transfer. When the oxygenator was so equipped and used with a line pressure of 300 mmHg, the blood outlet oxygen partial pressure was about 100 mmHg. This indicates that the device 10 of this invention would allow a decrease in the surface area of the standard Sarns oxygenator by almost 50 percent, while retaining approximately the same level of performance. This would allow both cost reduction, reduction in the exposure of blood to foreign surfaces, and a reduction in priming volume. These are generally known to be important patient concerns.

From the foregoing, it will be apparent that various modifications and changes may be made by those skilled in the art without departing from the spirit and scope of the invention described herein. Because these modifications and changes may be made by one skilled in the art and without departing from the scope and spirit of the invention, all matters shown and described are to be interpreted as illustrative and not in a limiting sense.

I claim:

1. A membrane oxygenator comprising:
   a housing having means defining a hollow portion communicating with first and second inlet means and first and second outlet means,
   said first inlet means for providing an incoming flow of blood into the oxygenator, said first outlet means for providing an outgoing flow of blood from the oxygenator, said second inlet means for providing an incoming flow of oxygenating gas to the oxygenator and said second outlet means for providing an outgoing flow of oxygenating gas from the oxygenator;

transfer membrane means comprising a hollow fiber bundle disposed within the hollow portion of the housing and defining oxygenating gas flow paths disposed between the first inlet means and the first outlet means and through individual fibers in said hollow fiber bundle, and defining blood flow paths disposed between the second inlet means and the second outlet means and around individual fibers in said hollow fiber bundle; and means for automatically maintaining the total pressure of the oxygenating gas at each point within the gas flow paths near yet below the total pressure of the blood on the other side of the transfer membrane means throughout the oxygenator, said automatic maintaining means being connected to said first and said second outlet means and comprising means for restricting the flow of oxygenating gas exiting the oxygenator through said first outlet means with the pressure of blood exiting the oxygenator through said second outlet means by providing a fluid with approximately the pressure of the blood exiting the oxygenator to exert pressure on the oxygenating gas exiting the oxygenator to raise the pressure of the oxygenating gas within the oxygenator near that of the exiting blood.

2. The membrane oxygenator according to claim 1 wherein the restricting means comprises:

a valve member comprising an inner tube having an inlet and an outlet in fluid communication with the first outlet means of the housing of the oxygenator; a housing receiving the inner tube; an inlet portion connecting the housing to the inner tube adjacent the inlet of the inner tube; and an outlet portion connecting the housing to the inner tube adjacent the outlet of the inner tube; and means for maintaining an above-ambient pressure in the area between the housing and the inner tube.

3. The membrane oxygenator according to claim 2 wherein the inner tube comprises a relatively soft and flexible material that offers negligible resistance to externally applied forces.

4. The membrane oxygenator according to claim 3 wherein the maintaining means comprises a tubing communicating the pressure of the exiting blood to the area between the valve housing and the inner tube.

5. The membrane oxygenator according to claim 4 further comprising a portion of the valve housing having means defining an aperture therethrough and wherein the tubing has an inlet in fluid communication with the second outlet means of the housing oxygenator and the tubing has an outlet in fluid communication with the aperture through the valve housing to provide means whereby the pressure in the area between the valve housing and the inner tube approaches that of the exiting blood.

6. The membrane oxygenator according to claim 5 further comprising a fluid transducer between the inlet and the outlet of the tubing to provide means whereby a fluid other than the blood exiting the oxygenator pressurizes the area between the valve housing and the inner tube.

7. A membrane oxygenator comprising:

a housing having inner surfaces defining a hollow portion, portions defining oxygenating gas inlet and outlet means for providing flow of oxygenating gas through the housing, and portions defining blood inlet and outlet means for providing flow of blood through the housing.

transfer membrane means comprising a hollow fiber bundle disposed within the hollow portion of the housing for transfer of oxygen from oxygenating gas to the blood defining oxygenating gas flow paths through individual fibers in said hollow fiber bundle and defining blood flow paths around individual fibers in said hollow fiber bundle; and means, connected between said oxygenating gas outlet means and said blood outlet means, for restricting the flow of oxygenating gas exiting the oxygenator through said oxygenating gas outlet means with the pressure of blood exiting the oxygenator through said blood outlet means by providing a fluid with approximately the pressure of the blood exiting the oxygenator to exert pressure on the oxygenating gas exiting the oxygenator to raise the pressure of the oxygenating gas within the oxygenator near that of the exiting blood.

8. A membrane oxygenator according to claim 7, wherein said restricting means comprises a valve member including an inner tube having inner surface portions and an outer periphery, an inlet and an outlet in fluid communication with the oxygenating gas outlet means of the housing of the oxygenator; a valve housing receiving the inner tube, and means for communicating the pressure of the flow of blood exiting the oxygenator through said blood outlet means to the outer periphery of the inner tube so that the pressure of blood exiting the oxygenator may raise the pressure of the oxygenating bas within the oxygenator near that of the exiting blood.

9. A membrane oxygenator comprising:

a housing having inner surfaces defining a hollow portion, portions defining oxygenating gas inlet and outlet means for providing flow of oxygenating gas through the housing, and portions defining blood inlet and outlet means for providing flow of blood through the housing, transfer membrane means comprising a hollow fiber bundle disposed within the hollow portion of the housing for transfer of oxygen from oxygenating gas to the blood defining oxygenating gas flow paths through individual fibers in said hollow fiber bundle and defining blood flow paths around individual fibers in said hollow fiber bundle; and a valve connected between said oxygenating gas outlet port and said blood outlet port, said valve including a tube for communicating the pressure of the flow of blood exiting the oxygenator through said blood outlet port to the flow of oxygenating gas exiting the oxygenator through said oxygenating gas outlet port, said valve restricting the flow of oxygenating gas exiting the oxygenator through said oxygenating gas outlet port with the pressure of blood exiting the oxygenator through said blood outlet port by providing fluid with approximately the pressure of the blood exiting the oxygenator to exert pressure on the oxygenating gas exiting the oxygenator to raise the pressure of the oxygenating gas within the oxygenator near that of the exiting blood.

10. A membrane oxygenator according to claim 9 wherein said valve includes an elastomeric inner tube.

11. A method of oxygenating blood comprising:

providing a membrane oxygenator comprising a housing having inner surfaces defining a hollow portion, transfer membrane means within the hollow portion, portions defining oxygenating gas inlet and outlet means, and portions defining blood inlet and outlet means, flowing oxygenating gas into the oxygenating gas inlet means, through the housing, and out through the oxygenating gas outlet means, flowing oxygen reduced blood into the blood inlet means, transferring oxygen from the oxygenating gas to the blood via the transfer membrane means within the housing and then flowing the blood out of the housing through the blood outlet means;

providing pressure approximately the same as the pressure of the blood flowing through the blood outlet means on the flow of oxygenating gas exiting the oxygenating gas outlet means to restrict the flow of oxygenating gas exiting the oxygenator through said oxygenating gas outlet means to raise the pressure of the oxygenating gas within the oxygenator near that of the exiting blood.

12. A method according to claim 11 wherein the step of providing pressure approximately the same as the pressure of the blood flowing through the blood outlet means to the flow of oxygenating gas exiting the oxygenating gas outlet means comprises the step of:

connecting a valve member between the oxygenating gas outlet means and the blood outlet means such that a change in blood pressure exiting the oxygenator changes the pressure of the oxygenating gas exiting the oxygenating gas outlet means.

* * * * *

UNITED STATES PATENT AND TRADEMARK OFFICE
CERTIFICATE OF CORRECTION

PATENT NO. : 5,152,964
DATED : October 6, 1992
INVENTOR(S) : Ronald J. Leonard

It is certified that error appears in the above-indentified patent and that said Letters Patent is hereby corrected as shown below:

Col. 8, line 32, delete "bas" insert --gas--.

Signed and Sealed this

Twelfth Day of April, 1994

Attest:

BRUCE LEHMAN

Attesting Officer

Commissioner of Patents and Trademarks